US012605305B2

(12) United States Patent
Zhang et al.

(10) Patent No.: US 12,605,305 B2
(45) Date of Patent: Apr. 21, 2026

(54) APPLICATION OF CITRATE METAL SALT IN ENDODONTIC TREATMENT, AND FORMULATION OBTAINED BY PREPARATION

(71) Applicant: KUNMING QINGCHENG HEALTHCARE TECH LTD., Kunming (CN)

(72) Inventors: Lei Zhang, Kunming (CN); Yu Sun, Kunming (CN); Kewang Lu, Kunming (CN); Yang Song, Kunming (CN); Yangfangyuan Long, Kunming (CN)

(73) Assignee: Kunming Qingcheng Healthcare Tech LTD., Kunming (CN)

( * ) Notice: Subject to any disclaimer, the term of this patent is extended or adjusted under 35 U.S.C. 154(b) by 403 days.

(21) Appl. No.: 18/025,339

(22) PCT Filed: Jul. 19, 2021

(86) PCT No.: PCT/CN2021/107143
§ 371 (c)(1),
(2) Date: Mar. 8, 2023

(87) PCT Pub. No.: WO2022/052631
PCT Pub. Date: Mar. 17, 2022

(65) Prior Publication Data
US 2024/0024207 A1    Jan. 25, 2024

(30) Foreign Application Priority Data
Sep. 10, 2020    (CN) .......................... 202010943885.4

(51) Int. Cl.
A61K 6/52        (2020.01)
A61K 6/69        (2020.01)
(52) U.S. Cl.
CPC . *A61K 6/52* (2020.01); *A61K 6/69* (2020.01)
(58) Field of Classification Search
CPC .................................... A61K 6/52; A61K 6/69
See application file for complete search history.

(56) References Cited

FOREIGN PATENT DOCUMENTS

| | | |
|---|---|---|
| CN | 101869534 A | 10/2010 |
| CN | 105213200 A | 1/2016 |
| CN | 105616169 A | 6/2016 |
| CN | 106132385 A | 11/2016 |
| CN | 108721121 A | 11/2018 |
| CN | 112022725 A | 12/2020 |
| MX | 2018006870 A | 12/2019 |
| WO | WO 01/34165 * | 5/2001 |
| WO | 101316516 * | 12/2008 |

OTHER PUBLICATIONS

International Search Report, and English Translation thereof, and Written Opinion for International Application No. PCT/CN2021/107143, mailed Oct. 28, 2021 (18 pages).
Chinese Office Action for Counterpart Chinese Application No. 202010943885.4, mailed Jun. 27, 2022 (29 pages).
Cruz-Filho et al., "Effect of Chelating Solutions on the Microhardness of Root Canal Lumen Dentin," Journ. Endod., vol. 37, No. 3, pp. 358-362, Mar. 2011 (5 pages).
Qiu Bingyi, "Encyclopedia of Cosmetic Chemistry and Technology," pp. 122-133, May 31, 1997 (13 pages). (English Abstract Only. See CN Office Action mailed Jun. 27, 2022).
Jingping Liang, "Clinical root canal therapy (Second edition)," pp. 93-99, Oct. 31, 2018 (8 pages). (English Abstract Only. See CN Office Action mailed Jun. 27, 2022).
Machado-Silveiro et al., "Decalcification of root canal dentine by citric acid, EDTA and sodium citrate," International Endodontic Journal, vol. 37, pp. 365-369, 2004 (5 pages).

* cited by examiner

*Primary Examiner* — Shirley V Gembeh
(74) *Attorney, Agent, or Firm* — Kagan Binder, PLLC

(57) ABSTRACT

Provided are an application of a citrate metal salt in endodontic treatment, and a formulation obtained by preparation; said citrate metal salt is used for removing a tarnished layer, and the citrate metal salt is lithium citrate, sodium citrate, potassium citrate, or magnesium citrate. The citrate metal salt is co-formulated with a citrate metal salt-compatible single-chain cationic antimicrobial agent, achieving results that are currently achieved only by alternating rinsing with EDTA-containing and sodium hypochlorite preparations in endodontic treatment.

8 Claims, 10 Drawing Sheets

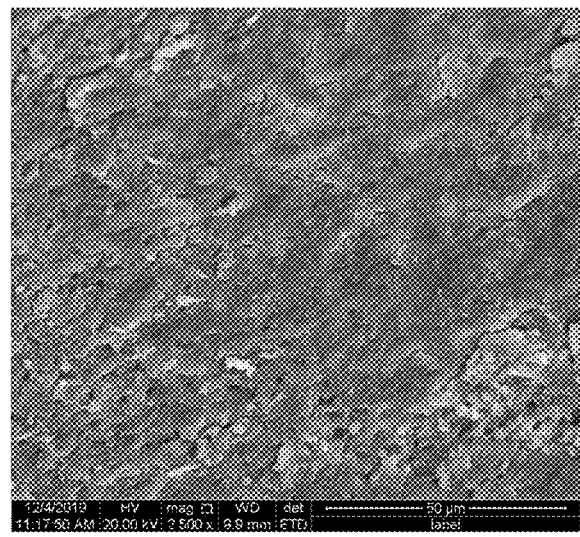
FIG. 4
FIG. 5
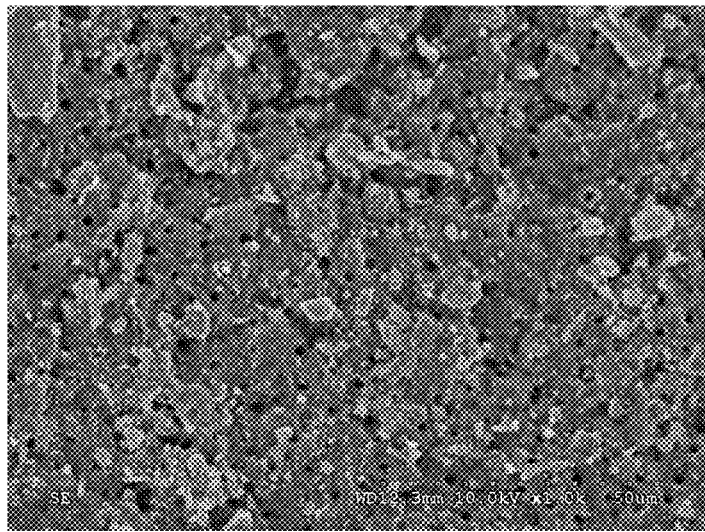
FIG. 6

APPLICATION OF CITRATE METAL SALT IN ENDODONTIC TREATMENT, AND FORMULATION OBTAINED BY PREPARATION

CROSS-REFERENCE TO RELATED APPLICATIONS

This application is a national stage for International Application PCT/CN2021/107143, filed on Jul. 19, 2021, and entitled "APPLICATION OF CITRATE METAL SALT IN ENDODONTIC TREATMENT, AND FORMULATION OBTAINED BY PREPARATION", which claims the priority benefit of Chinese Patent Application No. 202010943885.4 filed on Sep. 10, 2020.

TECHNICAL FIELD

The present disclosure relates to the technical field of root canal therapy, in particular relates to the use of a citrate metal salt in root canal therapy, and a formulation obtained by preparation.

BACKGROUND

A smear layer is a layer attached on root canal walls after root canal instrumentation. It consists of microcrystalline, organic particle debris, saliva, and bacteria. The dentine has a higher organic matter content than that of the enamel, so the smear layer formed when cutting the dentine is thicker than that formed when cutting enamel. The smear layer may enter the dentinal tubule to form a tubular plug, which cannot be removed by regular irrigation methods. The smear layer will hinder the bonding between the restoration and the canal wall. Meanwhile, the smear layer, due to its low surface free energy and hydrophilicity, is not conducive to the wetting and penetration of hydrophobic bonding agents on the dentin surface, thus affecting the bonding.

Root canal cleaning and shaping is the basis of disinfection and filling, but mechanical root canal preparation will produce a smear layer with a thickness of about 2-5 μm on the surface of the root canal. The smear layer covers the root canal wall and is composed of organic and inorganic matter such as necrotic tissues, bacteria, and dentin debris. The smear layer will prevent or delay the action of the disinfectant on the bacteria in the dentinal tubule, hinder the penetration and tight bonding of the root canal filling material to the root canal wall, so it is adverse to the control of infection and the tight sealing of the material. Hence, the extent to which the smear layer is removed from the root canal wall will directly affect the efficacy of root canal therapy. The function of the root canal irrigation solution is removing smear layer and disinfection. Currently, the sodium hypochlorite solution has become the most important bactericide for root canal irrigation due to its strong broad-spectrum bactericidal ability. However, sodium hypochlorite solution cannot remove the smear layer completely when used exclusively since it is not reactive with inorganic components in the smear layer. It needs to be used in combination with other root canal irrigation solutions. EDTA has been most commonly used in root canal irrigation solution since 1957. It is commonly used for irrigation with a concentration of 17% for 1-5 minutes. EDTA is a chelating agent that can form a soluble complex with $Ca^{2+}$ in hydroxyapatite, thereby achieving the purpose of dissolving inorganic substances in the smear layer. However, EDTA has irritation and allergy problems. Also, sodium hypochlorite would cause some adverse reactions during root canal therapy and have the potential to lead to very serious complications. The disadvantages of sodium hypochlorite include: unacceptable smell and taste, discoloring the clothing, difficulties in removing non-organic components in the smear layer, severe irritation and chemical burn. It also has difficulties in penetrating various positions of the root canal system. Most dangerously, sodium hypochlorite has cytotoxicity to the tissue which will cause a severe inflammatory response in the oral mucosa, and even have the potential to cause serious damage or even necrosis of the peri-apical tissue if it flows out of the apical foramen.

In addition, it has been reported in the literatures that organic or inorganic acids are used to remove the smear layer. However, since the mechanism is based on acidic erosion and dissolution of the dental hard tissue, it will cause serious demineralization of the dental tissue, reduce the strength of the dental hard tissue, and hinder the tight bonding of the root canal filling material to the root canal wall. Taking citric acid as an example, the pH values of 5% and 10% citric acid solutions are 1.93 and 1.91, respectively. Evidently, they are too acidic, and thus would have great acidic erosion and dissolution effect on the dental hard tissues. Therefore, it is quite necessary to find a root canal irrigation solution that can effectively remove the smear layer instead of EDTA.

Chinese patent CN105213200B discloses a lubricant for root canal therapy including sodium ethylene diamine tetra-acetate, citric acid, carbamide peroxide, hexadecyl trimethyl ammonium bromide, sodium carboxymethyl cellulose, glycerin and water. This patent claims that the lubricant has the effect of removing the smear layer of the root canal and good antibacterial effect. This formula has a content of citric acid up to 5-14%, thus the acidity of the lubricant is relatively strong. Removing the smear layer with the aid of the acidity of the organic acid would obviously lead to severe demineralization of the dental tissue and is therefore not optimal.

Chinese patent CN1633261A discloses an irrigation solution and application method thereof. The application method includes: irrigating the dental surface with a sterile solution containing a disinfectant, detergent and organic acid, to remove the smear layer. Obviously, this patented technology also utilizes the acidity of organic acids to remove the smear layer, and may also lead to the problem of serious demineralization of the dental tissue.

Chinese patent CN101012511B discloses a method of eliminating the influence of calcium ions in gold heap leaching production using sodium tripolyphosphate, and discloses the use of sodium tripolyphosphate to chelate $Ca^{2+}$ ion. However, in the present disclosure, it has been proved by multiple tests that sodium tripolyphosphate cannot be effective in removing the smear layer.

SUMMARY

The primary purpose of the present disclosure is to elucidate the use of a citrate metal salt in root canal therapy, aiming to mitigate the above-mentioned problems. After a long period of research by the inventors, it has been found that a specific citrate metal salt can effectively remove the smear layer, so as to replace EDTA-containing formulations currently used in root canal therapy and avoid the defect of using inorganic acids or organic acids. Using the citrate metal salt is safer and more reliable, providing a better choice for clinical root canal therapy.

The present disclosure discloses the following technology which use a citrate metal salt in root canal therapy, wherein the citrate metal salt is used for removing a smear layer, and the citrate metal salt is lithium citrate, sodium citrate, potassium citrate, or magnesium citrate.

In the present disclosure, the specific citrate metal salt is used to effectively remove the smear layer, so as to replace the treatment method of using EDTA-containing formulations currently used in root canal therapy and also avoid the defect of using inorganic acids or organic acids. Using the citrate metal salt is safer and more reliable, providing a better choice for clinical root canal therapy. In some embodiments, lithium citrate, sodium citrate, potassium citrate, or magnesium citrate, all of which belong to soluble citrate metal salts and have similar chemical properties, can effectively remove the smear layer. In the present disclosure, the citrate metal salt is preferably sodium citrate, but also can be other citrate metal salts mentioned above.

In the present disclosure, a citrate metal salt is formulated into a liquid, paste or gel with a pH value of 5.5-7.0. Numerous tests by the inventor reveal that a solution with a pH value of 5.5-7.0 has an obviously better effect of citrate metal salt for removing the smear layer than that of a solution that is alkaline, but if the pH is below 5.5, demineralization may occur.

The second purpose of the present disclosure is to disclose an effect of a citrate metal salt for removing the smear layer and destroy bacteria. By formulating the citrate metal salt with a single-chain cationic antibacterial agent compatible with the citrate metal salt into a stable and effective liquid, paste, or gel, to achieve the effect that can only be produced by currently using EDTA-containing formulations and sodium hypochlorite formulations. Also, combining the functions of the two necessary formulations in the current root canal therapy into one would avoid the adverse reactions caused by using EDTA and sodium hypochlorite. Therefore, this application method is safer and more effective.

The present disclosure adopts the following technical scheme: a single-chain cationic antibacterial agent compatible with the citrate metal salt is added to the citrate metal salt, and co-formulated into a liquid, paste, or gel.

In the present disclosure, the single-chain cationic antibacterial agent is: dodecyl to hexadecyl pyridinium chloride, such as dodecyl pyridinium chloride, tetradecyl pyridinium chloride, hexadecyl pyridinium chloride etc.; or decyl to hexadecyl dimethyl benzyl ammonium chloride, such as decyl dimethyl benzyl ammonium chloride, dodecyl dimethyl benzyl ammonium chloride, tetradecyl dimethyl benzyl ammonium chloride, hexadecyl dimethyl benzyl ammonium chloride, etc.; or decyl to octadecyl dimethyl benzyl ammonium bromide, such as decyl dimethyl benzyl ammonium bromide, dodecyl dimethyl benzyl ammonium bromide, tetradecyl dimethyl benzyl ammonium bromide, hexadecyl dimethyl benzyl ammonium bromide, octadecyl dimethyl benzyl ammonium bromide, etc.; or decyl to octadecyl trimethyl ammonium chloride, such as decyl trimethyl ammonium chloride, dodecyl trimethyl ammonium chloride, tetradecyl trimethyl ammonium chloride, hexadecyl trimethyl ammonium chloride, octadecyl trimethyl ammonium chloride, etc.; polydimethyl diallyl ammonium chloride; and acceptable combinations thereof, such as dodecyl pyridinium chloride used in combination with hexadecyl pyridinium chloride, etc.

In the present disclosure, a pH regulator is added to the liquid, paste, or gel to adjust the pH value of the liquid, paste, or colloid to 5.5-7.0. Since citrate metal salts are generally alkaline, leading to an alkaline pH value of the prepared liquid, paste, or gel, which will obviously affect the effect of removing the smear layer, it is necessary to introduce a pH regulator to adjust the pH value. The pH regulator may be an organic acid such as citric acid, hydrochloric acid or acetic acid or inorganic acid, on the basis of not affecting performance.

The third purpose of the present disclosure is to provide a formulation for removing a smear layer, which uses a citrate metal salt as the active ingredient. The formulation can effectively remove the smear layer, so as to replace the treatment method of using EDTA-containing formulations and sodium hypochlorite formulations alternately in the current root canal therapy and also avoid the defect of using inorganic acids or organic acids. The disclosed formulations are safer and more reliable, providing a better choice for clinical root canal therapy.

The present disclosure utilizes the following technical scheme: a formulation for removing a smear layer, wherein the formulation is a liquid, paste or gel with a pH value of 5.5-7.0 and is mainly formulated from a citrate metal salt, and the citrate metal salt is lithium citrate, sodium citrate, potassium citrate or magnesium citrate.

In some embodiments, the formulation contains a single-chain cationic antibacterial agent compatible with the citrate metal salt, and the single-chain cationic antibacterial agent is, one of or a mixture of any of, dodecyl to hexadecyl pyridinium chloride, polydimethyl diallyl ammonium chloride, decyl to hexadecyl dimethyl benzyl ammonium chloride, decyl to hexadecyl dimethyl benzyl ammonium bromide, decyl to octadecyl dimethyl benzyl ammonium bromide, or decyl to octadecyl trimethyl ammonium chloride.

In the present disclosure, when the formulation is a paste or gel, the carrier used is one of cellulose, carbomer, agar, chitosan, sodium alginate, stearic acid, hydrophilic vaseline, glyceryl stearic acid or cetyl alcohol, or the carrier used is one of, or a mixture of any of, poloxamer, glyceryl triacetate, PEG/PPG copolymer, glycol ethers and derivatives thereof, polyethylene glycol, polyethylene glycol/glyceryl hydroxystearate 40, or polysorbate.

In the present disclosure, the formulation consists of the following components: by mass percentage, no less than 5% of citrate metal salt, 0-5% of single-chain cationic antibacterial agent compatible with the citrate metal salt, with the balance of a solvent and/or an excipient. The solvent may be water or other acceptable solvents, and the excipient may be a thickener, a pH regulator, or a carrier, etc.

In some embodiments, in the method of using the formulation of the present disclosure, the formulation is applied to remove a smear layer for an application time of no more than 10 minutes. Tests by the inventor reveal that the solution shows a relatively better effect of citrate metal salt for removing the smear layer upon treating the root canal for 5 minutes. The solution cannot effectively remove the smear layer upon treating the root canal for 1 minute. The solution may cause slight dental damage upon treating the root canal for 10 minutes. Therefore, in order to avoid damage to the hard dental tissue, the application time should not exceed 10 minutes.

In summary, for the above-mentioned technical scheme, the present disclosure has the following beneficial effects:

a) The present disclosure provides use of a citrate metal salt in root canal therapy. After much research by the inventors, it has been found that a specific citrate metal salt can effectively remove the smear layer, so as to replace EDTA-containing formulations currently used in root canal therapy, and avoid the defect of using inorganic acids or organic acids. Using the citrate metal salt is safer and more reliable, providing a better choice for clinical root canal therapy;

b) In the present disclosure, the cationic antibacterial agents that may be compatible with citrate metal salts have been found, so as to prepare stable and effective formulations, thereby achieving the effect that can only be achieved by using EDTA-containing formulations and sodium hypochlorite formulations alternately in the current root canal therapy. The formulation of the present disclosure simplifies the doctor's operation steps and saves the time of therapy. Also, combining the functions of the two necessary formulations in the current root canal therapy into one would avoid the adverse reactions caused by using EDTA and sodium hypochlorite. Therefore, the formulation of the present disclosure is safer and more effective;

c) In the present disclosure, the pH range and application time for the formulation of the present disclosure to effectively remove the smear layer also have been found, providing a reference for clinical use.

BRIEF DESCRIPTION OF THE DRAWINGS

FIG. 4 is an SEM image of a root canal treated with normal saline for 1 minute.

FIG. 5 is an SEM image of a root canal treated with normal saline for 5 minutes.

FIG. 6 is an SEM image of a root canal treated with the solution of Formula 1 (pH: 5.15) for 1 minute.

DETAILED DESCRIPTION OF THE EMBODIMENTS

Figure 1:
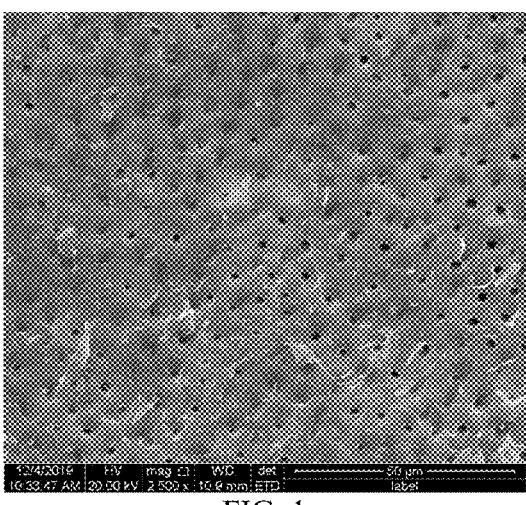
FIG. 1 is an SEM image of a root canal treated with a solution containing 17-22% EDTA-2Na for 1 minute.
Figure 2:
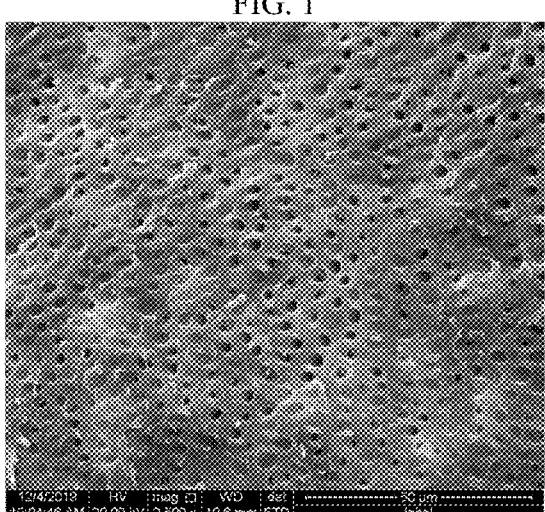
FIG. 2 is an SEM image of a root canal treated with a solution containing 17-22% EDTA-2Na for 5 minutes.
Figure 3:
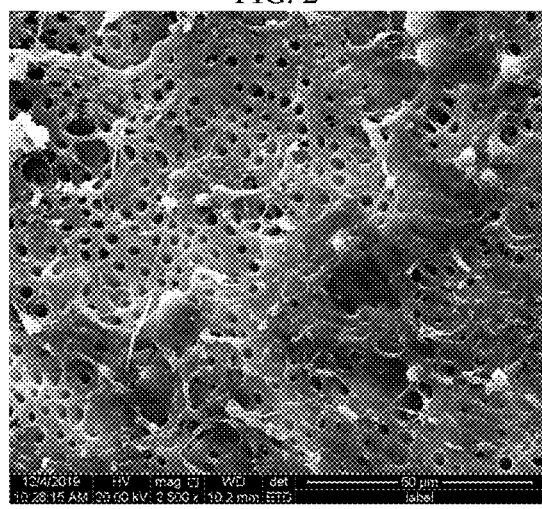
FIG. 3 is an SEM image of a root canal treated with a solution containing 17-22% EDTA-2Na for 10 minutes.

The present disclosure will be described in detail with reference to the accompanying drawings.

The purposes, technical solutions and advantages of the present disclosure will become more apparent and understandable by further describing the present disclosure in detail with reference to the accompanying drawings and examples. It should be understood that the specific examples illustrated herein are merely for explanation, and should not be deemed to limit the present disclosure.

I. Evaluation of the Effect of Removing Smear Layer In Vitro 1.1. Collection of Experimentally Isolated Teeth Healthy single premolars that need to be extracted for the purpose of clinical orthodontic extraction. Patient age: 14-25 years old. Inclusion criteria: single upright unobstructed root canal, fully developed apical foramen, no near-pulp caries or near-pulp fillings, no history of pulp therapy, no apical root resorption, no root fracture, and other defects, and no periodontal disease.

1.2. Treatment of Isolated Teeth

The soft tissue and calculus around the root of the isolated teeth were removed. The isolated teeth were cleaned and packed for high-temperature and high-pressure steam sterilization. Three sterilized isolated teeth were taken randomly and placed in 10 ml of BHI liquid culture medium, cultured at 37° C. for 24 h, and then taken out. With the naked eye, if the BHI liquid culture medium remains transparent, it is considered that the sterilization effect is reliable. If the BHI liquid culture medium is turbid, it is necessary to re-disinfect all samples and repeat the above steps. After confirmation of successful sterilization, the samples were stored at room temperature for later use.

1.3. Preparation of Root Canal

The pulp chamber of the isolated teeth confirmed to be successfully sterilized was opened using a high-speed handpiece with an emery ball bit with a diameter of 0.5 mm. After pulp extirpation, the root canal was dredged with an ISO standard #10 stainless steel hand K file, until the file tip that just penetrated the apical foramen was seen. The file was measured for length, from which 0.5 mm was subtracted to establish the working length of the root canal. Then the root canal preparation was performed using a Protaper Universal Engine with Nickel-titanium root canal file to 25/06. In the preparation process, upon instrument changing each time, a disposable sterile syringe (5 ml) with a replacement needle of 30G double-sided vented irrigation needle was placed at the position 3 mm from the root apex to irrigate the root canal with 0.9% normal saline for 1 min, and the root canal was washed by ultrasound oscillation using P5 ultrasonic equipment equipped with K15 for 40 s and then was dried with sterile 25/06 absorbent paper point.

7

1.4. Preparation of SEM Samples

After the preparation of the root canal, the tooth crown, cervical third and apical third were cut off using a low-speed cutting machine with water cooling, leaving the middle third (about 5 mm) for use. Grooves, which were about 2 mm deep but could not penetrate the root canal wall, were prepared on both the buccal and lingual sides of the isolated tooth root using a fissure bur. Then the tooth root was longitudinally divided into two parts along the long axis of the tooth root using a bone chisel, thus each root canal was divided into two parts, that is, two specimens were obtained from each tooth.

1.5. Experimental Processing

A commercially available "root canal lubrication solution" containing 17-22% EDTA-2Na, normal saline, and test samples (Formula 1-15 in Example 3) were selected and separately used for selective treatment of the specimens, according to the test design, for 1 minute, and/or 5 minutes, and/or 10 minutes. Then the specimens were washed 3 times with distilled water for 1 min each, washed twice with PBS solution, and air dried for 1 min. The specimens were then put in 2.5% glutaraldehyde solution for fixing at 4° C. for 2 h, then washed with PBS, and put in 40%, 50%, 60%, 70%, 80%, 90%, and 100% alcohol solutions in sequence for dehydration for 15 min. The specimens were then dried for 2 h, sprayed with gold, and observed under a scanning electron microscope. There were three samples in each group, and three areas of each sample were randomly selected to be observed by scanning electron microscopy for the coverage of the smear layer on the root canal wall.

1.6. Experimental Results

1. FIG. 1 to FIG. 5 show that the commercially available "root canal lubrication solution" was effective in removing the smear layer, but would cause great damage to the root canal if the root canal was treated for 10 min. Treating with normal saline for 1-5 min shows that normal saline was ineffective in removing the smear layer.

Figure 7:
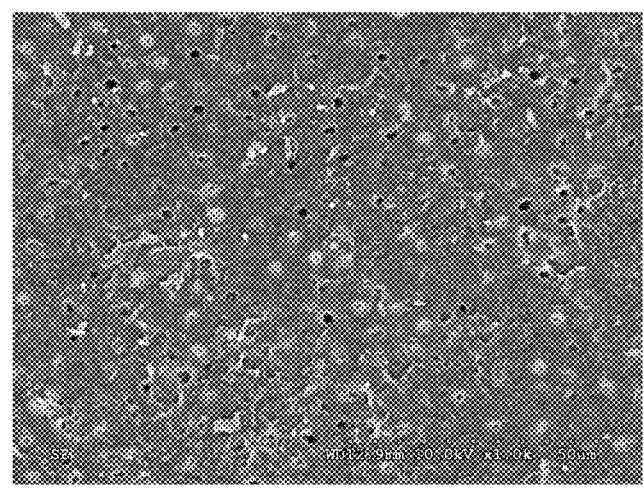
FIG. 7 is an SEM image of a root canal treated with the solution of Formula 2 (pH: 5.67) for 1 minute.
Figure 8:
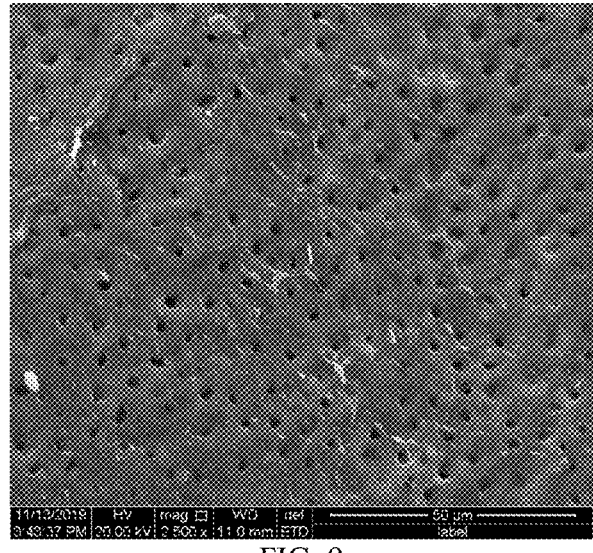
FIG. 8 is an SEM image of a root canal treated with the solution of Formula 3 (pH: 8.70) for 1 minute.

2. Comparison between FIG. 6 and FIG. 7 shows that Formula 1 was almost ineffective in removing the smear layer, while Formula 2 was effective in removing the smear layer. The reason is that sodium citrate is incompatible with didecyl dimethyl ammonium chloride, leading to the denaturation and failure of sodium citrate.

3. FIGS. 8, 12, 13, 14, and 15 correspond to Formula 3, Formula 5, Formula 6, and Formula 7, respectively. Their comparison shows sodium tripolyphosphate was worse effective than the commercially available "root canal lubrication fluid" on removing the smear layer.

4. FIG. 8 and FIGS. 12 to 15 show that sodium tripolyphosphate had a very poor effect of removing the smear layer and could not effectively remove the smear layer if the formulation contains no sodium citrate.

Figure 9:
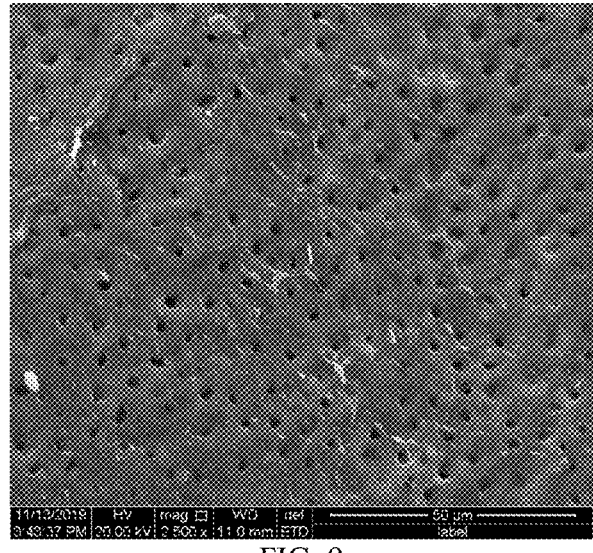
FIG. 9 is an SEM image of a root canal treated with the solution of Formula 4 (pH: 5.57) for 1 minute.
Figure 10:
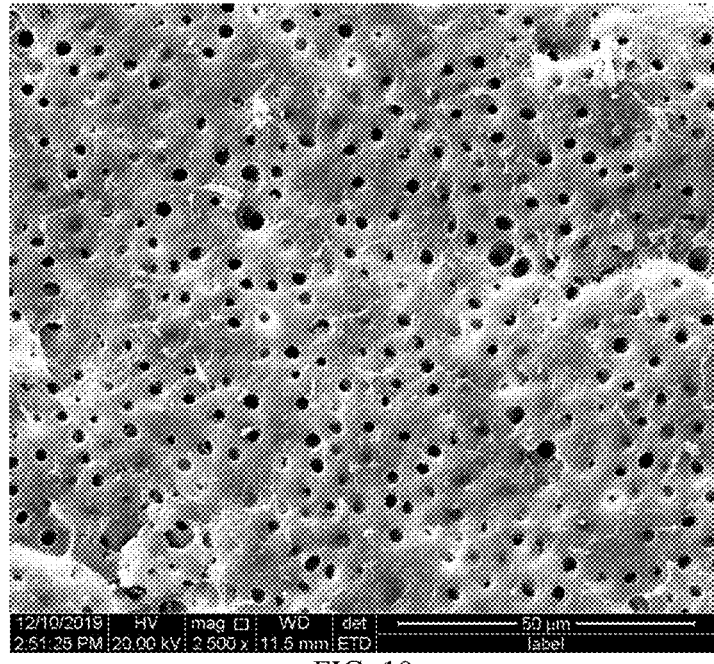
FIG. 10 is an SEM image of a root canal treated with the solution of Formula 4 (pH: 5.57) for 5 minutes.
Figure 11:
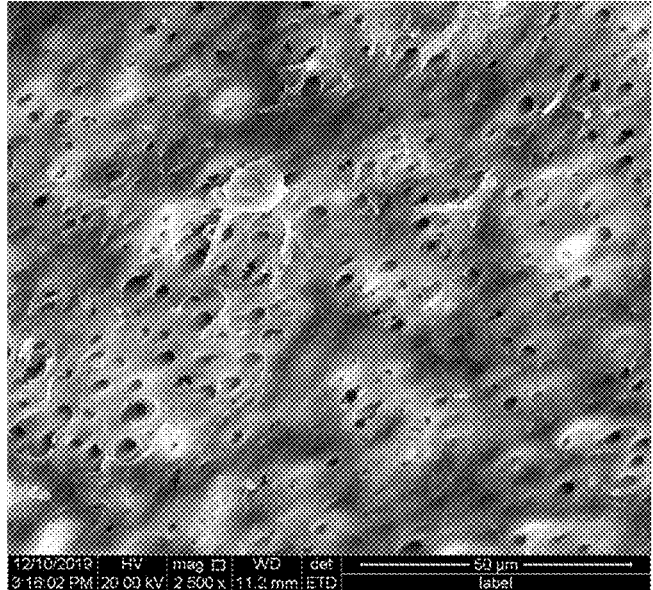
FIG. 11 is an SEM image of a root canal treated with the solution of Formula 4 (pH: 5.57) for 10 minutes.
Figure 12:
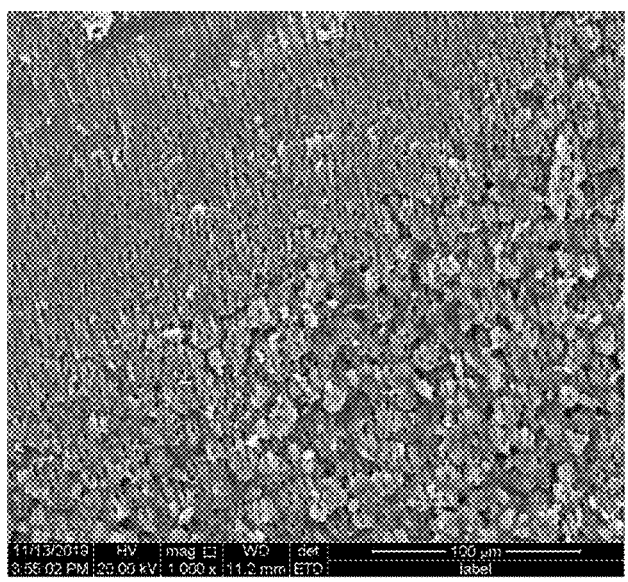
FIG. 12 is an SEM image of a root canal treated with the solution of Formula 5 (pH: 8.41) for 1 minute.
Figure 13:
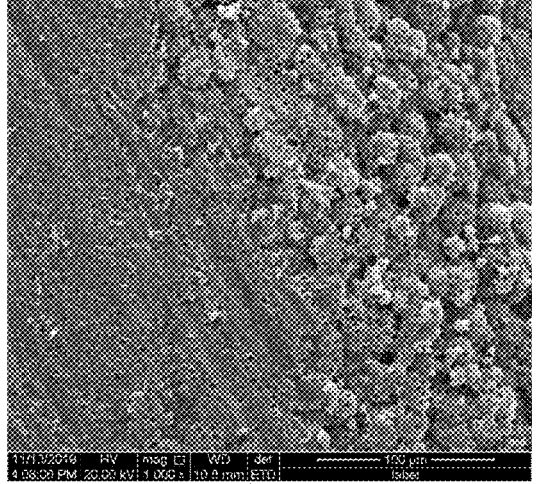
FIG. 13 is an SEM image of a root canal treated with the solution of Formula 6 (pH: 5.42) for 1 minute.
Figure 14:
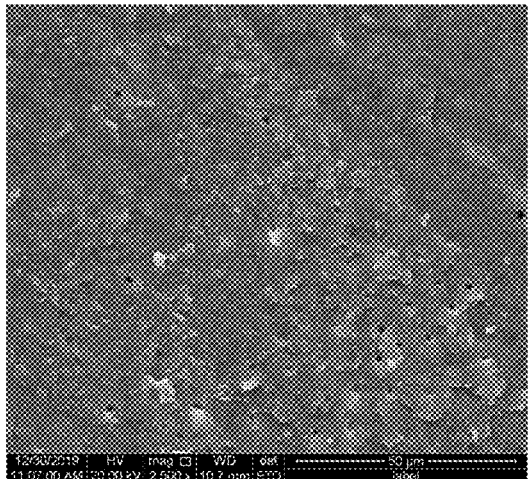
FIG. 14 is an SEM image of a root canal treated with the solution of Formula 7 (pH: 6.92) for 1 minute.

5. Comparison of FIG. 9, FIG. 10, and FIG. 11 show that there was obvious damage as shown in FIG. 11, proving that the root canal was damaged due to the treatment of the root canal with Formula 4 for 10 min. Also, the figures show that the removal effect of the smear layer was better if the root canal was treated for 5 min among the result of treating the root canal with Formula 4 for 1 min, 5 min, or 10 min.

Figures 15, 16:
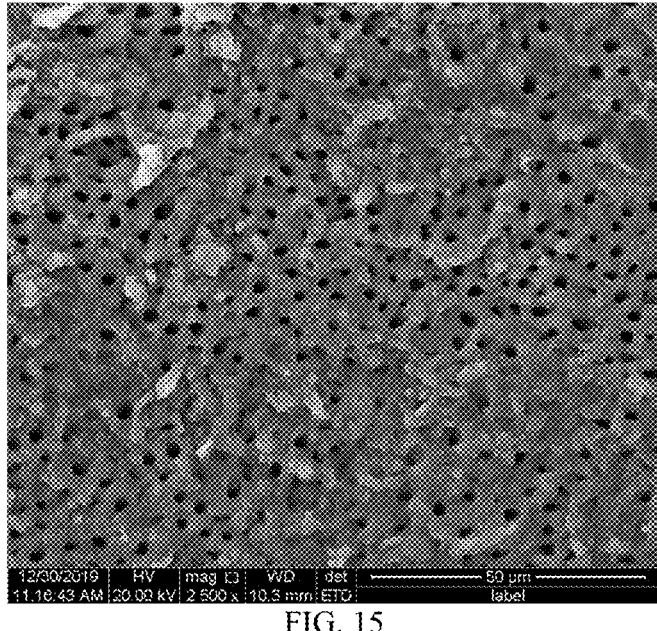
FIG. 15 is an SEM image of a root canal treated with the solution of Formula 7 (pH: 6.92) for 5 minutes.
FIG. 16 is an SEM image of a root canal treated with the solution of Formula 8 (pH: 6.79) for 1 minute.
Figure 17:
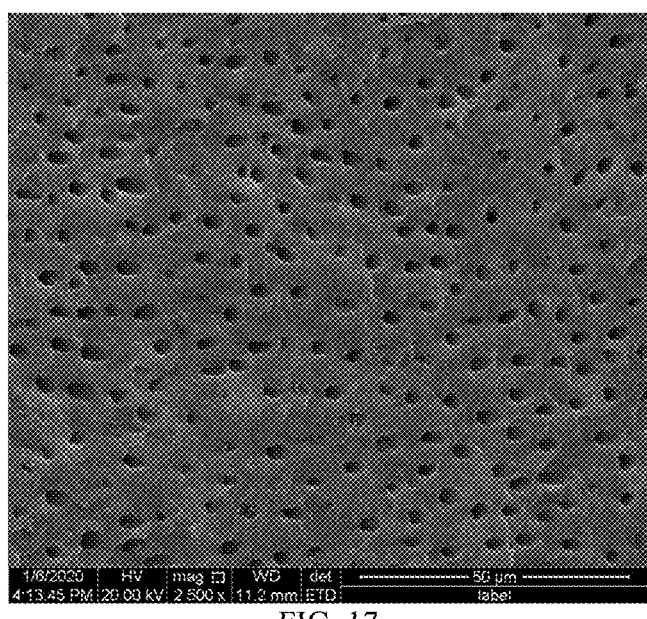
FIG. 17 is an SEM image of a root canal treated with the solution of Formula 8 (pH: 6.79) for 5 minutes.
Figure 18:
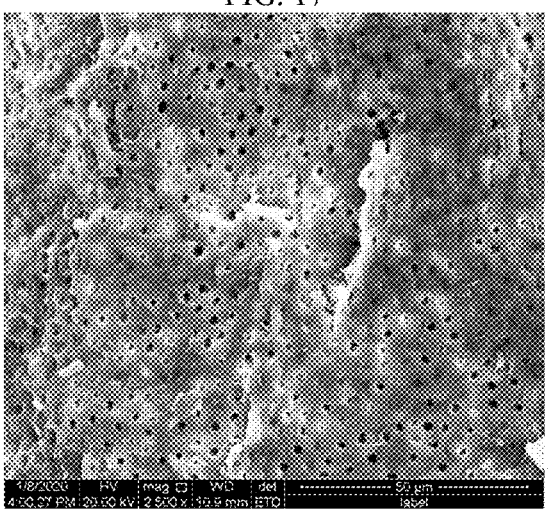
FIG. 18 is an SEM image of a root canal treated with the solution of Formula 8 (pH: 6.79) for 10 minutes.
Figure 19:
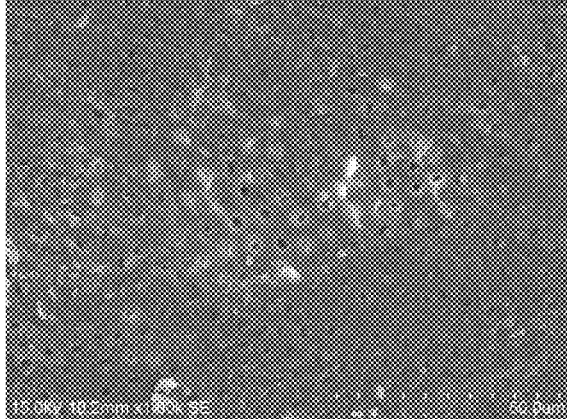
FIG. 19 is an SEM image of a root canal treated with the solution of Formula 9 (pH: 6.88) for 1 minute.
Figure 20:
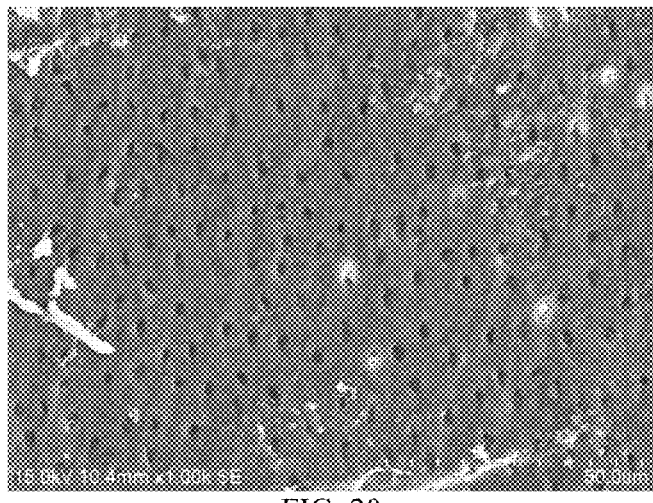
FIG. 20 is an SEM image of a root canal treated with the solution of Formula 9 (pH: 6.88) for 5 minutes.
Figure 21:
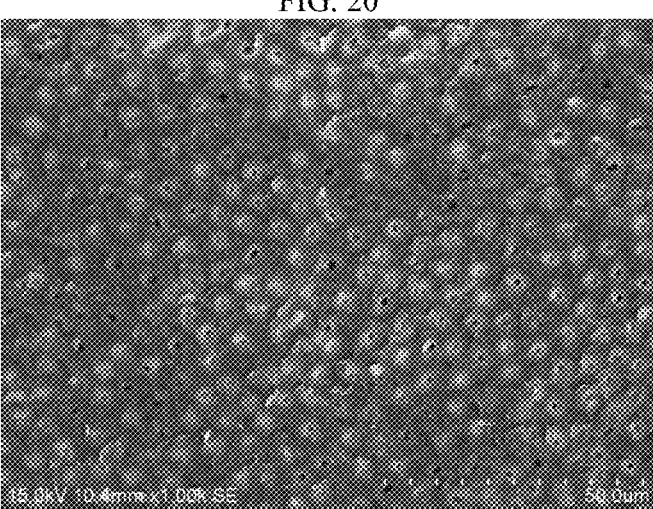
FIG. 21 is an SEM image of a root canal treated with the solution of Formula 10 (pH: 7.25) for 1 minute.

6. Comparison of FIG. 16, FIG. 17 and FIG. 18 show that there was obvious damage as shown in FIG. 18, proving that the root canal was damaged due to the treatment of the root canal with Formula 8 for 10 min. Also, the figures show that the removal effect of the smear layer was better when if the root canal was treated for 5 min among the result of treating the root canal with Formula 8 for 1 min, 5 min, or 10 min.

Figure 22:
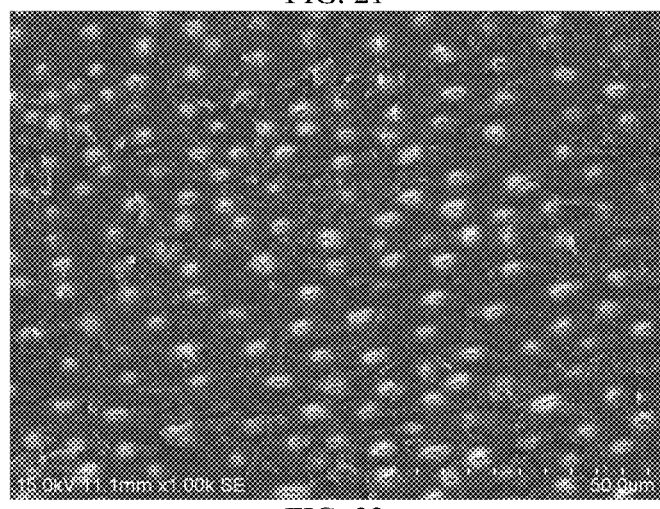
FIG. 22 is an SEM image of a root canal treated with the solution of Formula 10 (pH: 7.25) for 5 minutes.
Figure 24:
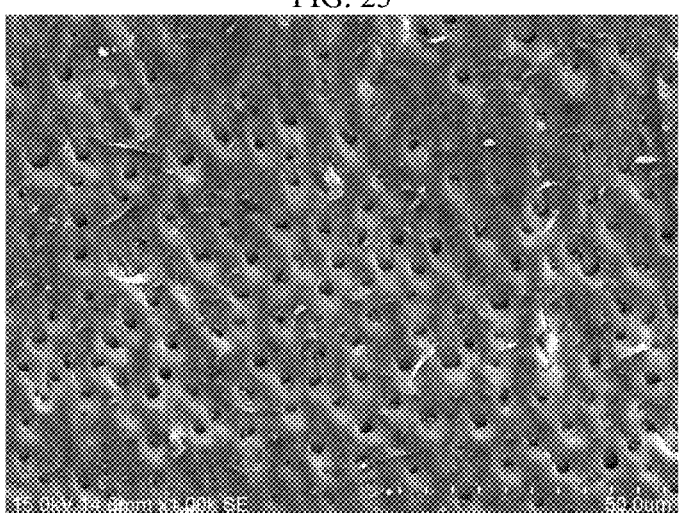
FIG. 24 is an SEM image of a root canal treated with the solution of Formula 12 (pH: 5.88) for 5 minutes.

7. FIG. 22 and FIG. 24 correspond to Formula 10 and Formula 12, respectively. The comparison between FIG. 22 and FIG. 24 prove that the addition of potassium pyrophosphate could not improve the effect of the formulation on removing the smear layer.

8. Comparison between FIG. 22 and FIG. 24 show that as for Formula 10 and Formula 12 which contain the same amount of sodium citrate, the effect of removing the smear layer of the solution with an acidic pH was better than that with an alkaline pH.

Figure 25:
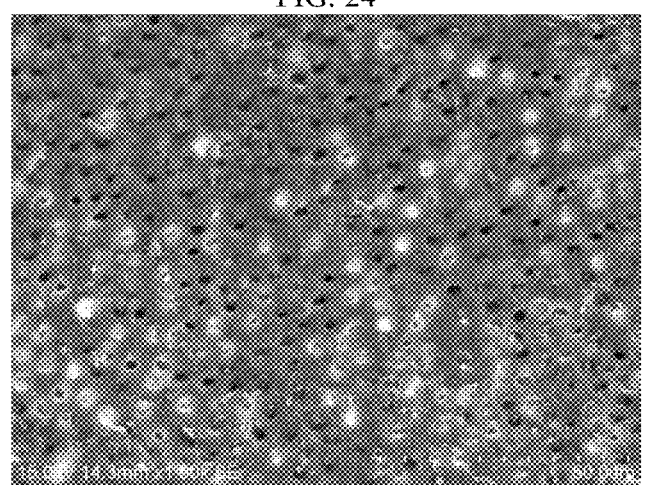
FIG. 25 is an SEM image of a root canal treated with the solution of Formula 13 (pH: 5.83) for 5 minutes.

9. FIG. 17, FIG. 24, and FIG. 25 correspond to Formula 8, Formula 12, and Formula 13, respectively, showing that the effect of removing the smear layer of the solution containing sodium citrate was equivalent to that of the commercially available "root canal lubricant", as compared with FIG. 2.

Figure 23:
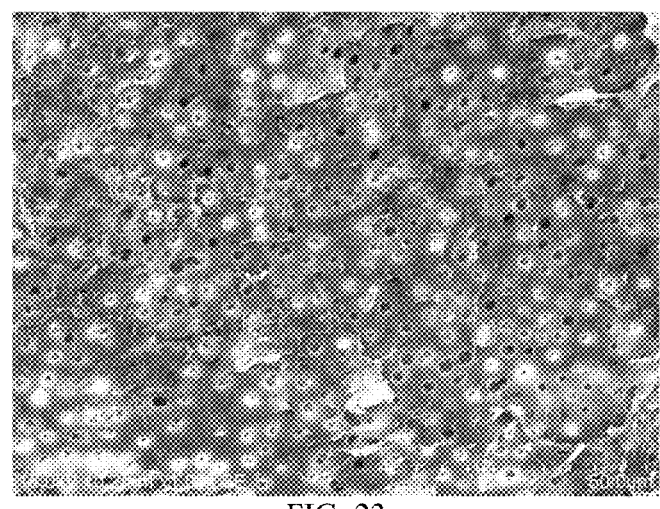
FIG. 23 is an SEM image of a root canal treated with the solution of Formula 11 (pH: 5.21) for 5 minutes.
Figure 26:
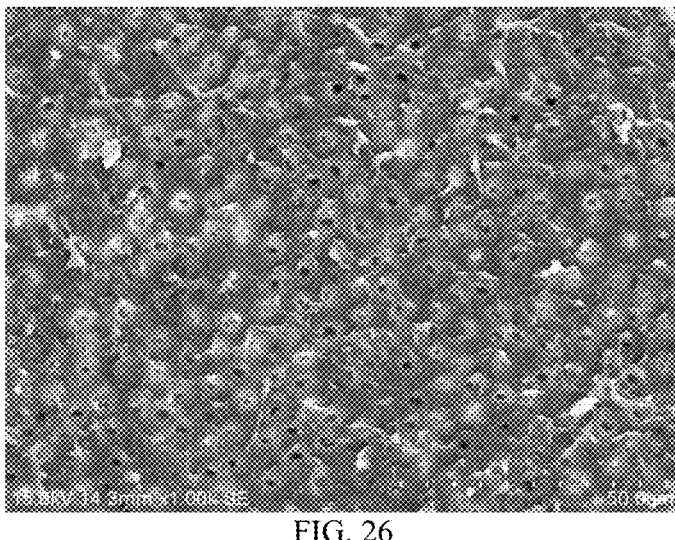
FIG. 26 is an SEM image of a root canal treated with the solution of Formula 14 (pH: 5.80) for 5 minutes.

10. FIG. 23 and FIG. 26 corresponded to Formula 11 and Formula 14, respectively, their comparison shows that sodium tripolyphosphate was not helpful for sodium citrate to improve the effect of removing the smear layer.

Figure 27:
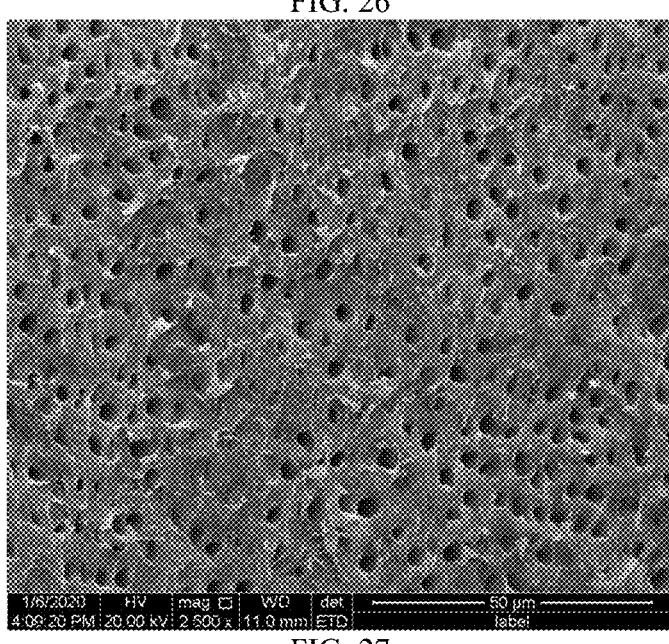
FIG. 27 is an SEM image of a root canal treated with the solution of Formula 15 (pH: 6.12) for 5 minutes.

11. FIG. 27 corresponded to Formula 15, showing that an aqueous solution of sodium citrate could remove the smear layer, further proving that the metal salt of citrate was capable of effectively removing the smear layer.

II. Tests of Citric Acid, Citrate Metal Salt for Compatibility with Cationic Antibacterial Agent 2.1. Major Materials Materials to be tested: sodium citrate, potassium citrate, lithium citrate, citric acid, EDTA-2Na.

Cationic antibacterial agents to be tested: didecyl dimethyl ammonium chloride, didecyl dimethyl ammonium acetate, hexadecyl pyridinium chloride, polydimethyl diallyl ammonium chloride, dodecyl dimethyl benzyl ammonium chloride, dodecyl dimethyl benzyl ammonium bromide, dodecyl trimethyl ammonium chloride, chlorhexidine acetate, polyhexamethylene biguanide hydrochloride, polyhexamethyl guanidine hydrochloride, N-cocoyl-L-arginine ethyl ester-DL-pyrrolidone carboxylate.

2.2. Test Method

Each of the citric acid metal salts to be tested was prepared as a 20% aqueous solution; the citric acid to be tested was prepared as a 20% aqueous solution; the EDTA-2Na to be tested was prepared as a 10% aqueous solution; and the cationic antibacterial agent to be tested was prepared as a 0.2% aqueous solution. Each of the prepared aqueous solutions of citrate metal salt (or citric acid aqueous solutions) was mixed with each of the prepared aqueous solutions of cationic antibacterial agent to be tested at a ratio of 1:1.

All the mixed solutions were stored at room temperature in dark and left standing for 7 days before observation.

2.3. Test Results

TABLE 1

| Compatibility with sodium citrate solution | |
| --- | --- |
| Compound | Phenomenon |
| didecyl dimethyl ammonium chloride | + |

TABLE 1-continued

| Compatibility with sodium citrate solution | |
|---|---|
| Compound | Phenomenon |
| didecyl dimethyl ammonium acetate | + |
| hexadecyl pyridinium chloride | − |
| polydimethyl diallyl ammonium chloride | − |
| dodecyl dimethyl benzyl ammonium chloride | − |
| dodecyl dimethyl benzyl ammonium bromide | − |
| dodecyl trimethyl ammonium chloride | − |
| chlorhexidine acetate | + |
| chlorhexidine gluconate | + |
| polyhexamethylene biguanide hydrochloride | + |
| polyhexamethyl guanidine hydrochloride | + |
| N-cocoyl-L-arginine ethyl ester-DL-pyrrolidone carboxylate | + |

Note:
"+" represented turbidity, precipitation, agglomeration occurred;
"−" represented transparent and clear solution.

TABLE 2

| Compatibility with potassium citrate solution | |
|---|---|
| Compound | Phenomenon |
| didecyl dimethyl ammonium chloride | + |
| didecyl dimethyl ammonium acetate | + |
| hexadecyl pyridinium chloride | − |
| polydimethyl diallyl ammonium chloride | − |
| dodecyl dimethyl benzyl ammonium chloride | − |
| dodecyl dimethyl benzyl ammonium bromide | − |
| dodecyl trimethyl ammonium chloride | − |
| chlorhexidine acetate | + |
| chlorhexidine gluconate | + |
| polyhexamethylene biguanide hydrochloride | + |
| polyhexamethyl guanidine hydrochloride | + |
| N-cocoyl-L-arginine ethyl ester-DL-pyrrolidone carboxylate | + |

Note:
"+" represented turbidity, precipitation, agglomeration occurred;
"−" represented transparent and clear solution.

TABLE 3

| Compatibility with lithium citrate solution | |
|---|---|
| Compound | Phenomenon |
| didecyl dimethyl ammonium chloride | + |
| didecyl dimethyl | + |

TABLE 3-continued

| Compatibility with lithium citrate solution | |
|---|---|
| Compound | Phenomenon |
| ammonium acetate | |
| hexadecyl pyridinium chloride | − |
| polydimethyl diallyl ammonium chloride | − |
| dodecyl dimethyl benzyl ammonium chloride | − |
| dodecyl dimethyl benzyl ammonium bromide | − |
| dodecyl trimethyl ammonium chloride | − |
| chlorhexidine acetate | + |
| chlorhexidine gluconate | + |
| polyhexamethylene biguanide hydrochloride | + |
| polyhexamethyl guanidine hydrochloride | + |
| N-cocoyl-L-arginine ethyl ester-DL-pyrrolidone carboxylate | + |

Note:
"+" represented turbidity, precipitation, agglomeration occurred;
"−" represented transparent and clear solution.

TABLE 4

| Compatibility with citric acid solution | |
|---|---|
| Compound | Phenomenon |
| didecyl dimethyl ammonium chloride | + |
| didecyl dimethyl ammonium acetate | + |
| hexadecyl pyridinium chloride | − |
| polydimethyl diallyl ammonium chloride | − |
| dodecyl dimethyl benzyl ammonium chloride | − |
| dodecyl dimethyl benzyl ammonium bromide | − |
| dodecyl trimethyl ammonium chloride | − |
| chlorhexidine acetate | + |
| chlorhexidine gluconate | + |
| polyhexamethylene biguanide hydrochloride | + |
| polyhexamethyl guanidine hydrochloride | + |
| N-cocoyl-L-arginine ethyl ester-DL-pyrrolidone carboxylate | + |

Note:
"+" represented turbidity, precipitation, agglomeration occurred;
"−" represented transparent and clear solution.

TABLE 5

| Compatibility with EDTA-2Na solution | |
|---|---|
| Compound | Phenomenon |
| didecyl dimethyl ammonium chloride | + |
| didecyl dimethyl ammonium acetate | + |

TABLE 5-continued

| Compatibility with EDTA-2Na solution | |
| --- | --- |
| Compound | Phenomenon |
| hexadecyl pyridinium chloride | – |
| polydimethyl diallyl ammonium chloride | – |
| dodecyl dimethyl benzyl ammonium chloride | – |
| dodecyl dimethyl benzyl ammonium bromide | – |
| dodecyl trimethyl ammonium chloride | – |
| chlorhexidine acetate | + |
| chlorhexidine gluconate | + |
| polyhexamethylene biguanide hydrochloride | + |
| polyhexamethyl guanidine hydrochloride | + |
| N-cocoyl-L-arginine ethyl ester-DL-pyrrolidone carboxylate | + |

Note:
"+" represented turbidity, precipitation, agglomeration occurred;
"–" represented transparent and clear solution.

2.4. Conclusion of the Test

Citric acid solution could be compatible with all the cationic antibacterial agents to be tested above, while sodium citrate, potassium citrate, and lithium citrate are only compatible with hexadecyl pyridinium chloride, dodecyl trimethyl ammonium chloride, polydimethyl diallyl ammonium chloride, dodecyl dimethyl benzyl ammonium chloride, and dodecyl dimethyl benzyl ammonium bromide, and they are hardly compatible with double-chain cationic antibacterial agents. EDTA-2Na is compatible with other cationic antibacterial agents except didecyl dimethyl ammonium chloride, didecyl dimethyl ammonium acetate, chlorhexidine acetate, and chlorhexidine gluconate.

III. MIC Determination of Mixed Bacteria 3.1. Preparation of Mixed Bacterial Suspension The seed liquid of *Enterococcus faecalis* (*Enterococcus faecalis* standard strain ATCC19433) was resuscitated and inoculated into 10 mL of BHI liquid medium, the seed liquids of *Fusobacterium nucleatum* (*Fusobacterium nucleatum* subsp. ATCC25586) and *Prevotella melaninogenica* (*Prevotella melaninogenica* 0110P) were each resuscitated and inoculated into 10 mL of BHI liquid medium containing hemin and vitamin K1. They were cultured anaerobically at 37° C. overnight. The next day, the bacterial solutions were shaken to suspend the bacteria uniformly, and diluted in a fresh BHI medium at a ratio of bacterial solution:BHI liquid medium of 1:9, then cultured anaerobically at 37° C. overnight. The next day, 1 ml of each of the three bacterial solutions was collected and cultured anaerobically at 37° C. until logarithmic growth phase, then the three bacterial solutions were each adjusted to a concentration of $1 \times 10^7$ CFU/mL, and then each bacterial solution was mixed at a ratio of 1:1 to form a mixed bacterial suspension.

3.2. Determination of MIC of Experimental Sample Solution

The mixed bacterial suspension prepared in 1.1 was diluted to $10^6$ CFU/mL, and 0.5 ml of the mixed bacterial suspension was added to each 48-well plate. After diluting the stock solution of the sample solution (Formula 4) in equal ratio, 0.5 ml of the diluted solutions were added to the plate wells in the order from low concentration to high concentration. Then the plate was placed in an incubator at 37° C. for anaerobic cultivation for 48 h. After that, with the naked eye, the concentration of the diluted solution at which the liquid was clear without the growth of pellet in the well of the plate is determined as the lowest drug concentration.

3.3. MIC results of Sample Solution

The MIC of the experimental sample solution was obtained from the sample solutions (Formula 4) diluted by 8 times in an equal ratio. In this system, the MIC of the solution containing dodecyl dimethyl benzyl ammonium chloride against the mixed bacterial suspension was about 3.9 PPM.

IV. Evaluation of the Irrigation Effect of Infected Root Canal In Vitro 4.1. Collection of Isolated Teeth 36 healthy single premolars that need to be extracted due to clinical orthodontic extraction were selected. Patient age: 14-25 years old. Inclusion criteria: single upright unobstructed root canal, fully developed apical foramen, no near-pulp caries or near-pulp fillings, no history of pulp therapy, no apical root resorption, no root fracture and other defects, no periodontal disease.

4.2. Treatment of Isolated Teeth

The soft tissues around the root and calculus of the isolated teeth were removed. The isolated teeth were cleaned, placed in normal saline, and restored in a refrigerator at 4° C. for later use. Before the experimentation, using a low-speed cutting machine with water cooling, the pulp chamber was completely opened using a high-speed hand piece with an emery ball bit with a diameter of 0.5 mm. After the pulp extirpation, an ISO standard #10 hand stainless steel K file was used to probe whether it was unobstructed from the root canal to the apical foramen. If confirmed, the tooth was packed for high-temperature and high-pressure steam sterilization. Three sterilized isolated teeth were taken randomly and placed into 10 ml of BHI liquid culture medium, cultured at 37° C. for 24 h, and then taken out. With the naked eye, if the BHI liquid culture medium remains transparent, it is confirmed that the sterilization effect is reliable. If the BHI liquid culture medium is turbid, it is necessary to re-disinfect all samples and repeat the above steps. After confirmation of successful sterilization, the samples were stored at room temperature for later use.

4.3. Preparation of Multi-Microorganism Infected Root Canal Model

The sterilized isolated teeth were taken out in a sterile table. The mixed bacterial solution was injected into the root canal of each tooth under pressure using a disposable sterile syringe (5 ml) with a replacement needle of 30G double-sided vented irrigation needle. The injection was stopped when the bacterial solution was seen leaking from the apical foramen. The isolated teeth were placed into a 24-well plate with each well filled with 2 ml of the pre-prepared mixed bacterial solution to submerge the tooth root completely. The bacterial solution was cultured under an anaerobic condition at 37° C. for 21 days with a fresh medium replaced every other day.

4.4. Preparation and Sampling of Infected Root Canal Model

After culturing for 21 days, the isolated teeth were taken out, and the isolated teeth were stood vertically, with the root apex being downward, and the root canal orifice loaded with a small sterile cotton ball and temporarily sealed with a hydrophilic temporary restorative (GC Dental Products). The surface of the tooth root was naturally dried for 1 min, and the entire surface of the vertical tooth root was coated using a cotton swab with a proper amount of Ci (KO-BAYASHI, Japan) plaque disclosing agent, which provided color development of the biofilm on the surface of the tooth root. Then the colored layer was scraped off from the surface of the tooth root using a sterilized periodontal curette. Then the tooth root was wiped with iodophor 3 times, and naturally dried for later use. Apical 3 mm of the root apex was etched with 35% BISCO etchant for 30 seconds. After water irrigating and drying, it was coated with a 3M Single Bond universal adhesive, which was then cured using a photosensitive lamp. Subsequently, the apical foramen was covered by a uniform coating of 3M XT flowable resin A2 color with a thickness of 0.5 mm, which was then cured using the photosensitive lamp. The temporary restorative at the root canal orifice and then the small cotton ball was removed using a probe, and the root canal was dredged with an ISO standard #10 stainless steel hand K file, until the file tip that just penetrated the apical foramen was seen. Then the root canal preparation was performed using a Protaper Universal Engine with Nickel-titanium root canal file to 25/06. In the preparation process, upon instrument changing each time, a disposable sterile syringe (5 ml) with a replacement needle of 30G double-sided vented irrigation needle was placed at the position 3 mm from the root apex to irrigate the root canal with 0.9% normal saline for 1 min, and the root canal was washed by ultrasound oscillation using P5 ultrasonic equipment equipped with K15 for 40 s.

4.5. Experimental Grouping and Processing

After the preparation, final irrigation was performed on the root canal. Then the 36 isolated teeth were randomly divided into 3 groups: Group A for negative control, in which the treatment liquid was normal saline, and the treatment time was 1 min; Group B for positive control, in which the treatment liquid was 5.25% sodium hypochlorite, and the treatment time is 1 min; and Group C for testing, in which the treatment time was 1 min. After the treatment for each of the teeth, the root canal was dried using the sterile 25/06 absorbent paper point, filled up with 0.9% saline and left standing for 1 min. The sterile 2506 absorbent paper point was placed into the root canal of each of the teeth in the working length, and kept in contact with the root canal wall for 1 min to dry the root canal. Then the paper point was taken out and placed into a 24-well plate with each well filled with 1 ml BHI liquid medium. Then the 36 paper points were incubated anaerobically at 37° C. for 48 hours. After shaking for 1 min to suspend the bacteria uniformly, the culture solution, sampled 100 μl in triplicate from each paper point, was spread on three dishes of BHI AGAR medium, that is, the culture solution for each of the teeth was spread on three culture dishes, and thus there were a total of 108 culture dishes on which samples were spread. The culture dishes were incubated anaerobically at 37° C. for 1 week. The growth of colonies on the plate was examined, with CFU counting and quantitative analysis performed.

4.6. Experimental Results

| Group | Bacteria observed | Bacteria unobserved | Total |
|---|---|---|---|
| A | 8 | 4 | 12 |
| B | 3 | 9 | 12 |
| C | 3 | 9 | 12 |

4.7. Conclusion

The sterilizing effect of irrigating the infected root canal with the stock solution of the sample solution (Formula 4) for 1 min in vitro was almost the same as that of irrigating with 5.25% sodium hypochlorite solution for 1 min, indicating that the formulation prepared by mixing the citrate metal salt with compatible cationic antibacterial agent has the same effect in root canal therapy as that obtained with sodium hypochlorite solution currently used, and could replace the method in current root canal therapy.

V. Specific Implementation

Example 1

The product was in a liquid state and was prepared with the following raw materials by weight percentage: 0.1% of dodecyl dimethyl benzyl ammonium chloride, 20.0% of sodium citrate, 1.0% of acetic acid, and deionized water as the balance.

Formulation:

1. The above-mentioned raw materials were taken according to the proportioning ratio, and mixed uniformly to obtain a homogeneous solution at room temperature.

2. The homogeneous solution was packaged using a filling machine into a suitable container to obtain the finished product.

Example 2

The product is a gel and prepared with the following raw materials by weight percentage: 0.1% of dodecyl dimethyl benzyl ammonium chloride, 20.0% of sodium citrate, 1.0% of acetic acid, 3.0% of hydroxypropyl methylcellulose as a thickener, and deionized water as the balance.

Formulation:

1. The above-mentioned raw materials were taken according to the proportioning ratio, and mixed uniformly.

2. Hydroxypropyl methylcellulose was dissolved in hot water above 70° C., fully dispersed and swelled, and cooled to obtain colloid A.

3. The remaining raw materials were prepared at room temperature into a homogeneous solution, which was added to the colloid A.

4. The homogeneous solution was packaged with a filling machine into a suitable container to obtain the finished product.

Example 3

The raw materials and their mass ratios of 15 formulas are listed in the following table. For each formula, its raw materials were taken according to the mass ratio, to prepare a homogeneous, colorless and transparent solution according to the formulation method of Example 1.

TABLE 6

| | | | | | | Raw material | | | | | | |
|---|---|---|---|---|---|---|---|---|---|---|---|---|
| Formula | CANa | CA | BZK | PA | AA | STPP | CPC | DDPC | PPP | PHMB | water to 100% | pH value |
| Formula 1 | 5.0 | 1.0 | — | — | — | — | 0.1 | 0.2 | — | — | 100 | 5.15 |
| Formula 2 | 5.0 | 0.5 | — | — | — | — | 0.1 | — | — | — | 100 | 5.67 |
| Formula 3 | — | — | — | — | — | 10.0 | — | — | — | 0.1 | 100 | 8.70 |
| Formula 4 | 10.0 | 1.5 | 0.1 | — | — | — | — | — | — | — | 100 | 5.57 |
| Formula 5 | — | — | — | — | — | 10.0 | 0.1 | — | — | — | 100 | 8.41 |
| Formula 6 | — | 2.3 | — | — | — | 10.0 | — | — | — | 0.1 | 100 | 5.42 |
| Formula 7 | — | — | 0.05 | 0.26 | — | 12.0 | — | — | — | — | 100 | 6.92 |
| Formula 8 | 17.0 | 0.17 | 0.05 | — | — | — | — | — | — | — | 100 | 6.79 |
| Formula 9 | 25.0 | 0.1 | 0.1 | — | — | — | — | — | — | — | 100 | 6.88 |
| Formula 10 | 20.0 | 0.12 | 0.1 | — | — | — | — | — | 1.0 | — | 100 | 7.25 |
| Formula 11 | 15.0 | — | 0.1 | — | 2.2 | — | — | — | — | — | 100 | 5.21 |
| Formula 12 | 20.0 | — | 0.1 | — | 1.0 | — | — | — | — | — | 100 | 5.88 |
| Formula 13 | 25.0 | — | 0.1 | — | 1.2 | — | — | — | — | — | 100 | 5.83 |
| Formula 14 | 12.0 | — | 0.1 | — | 1.6 | 5.0 | — | — | — | — | 100 | 5.80 |
| Formula 15 | 15.0 | — | — | — | 2.0 | — | — | — | — | — | 100 | 6.12 |

In Table 6, CANa: sodium citrate; CA: citric acid; BZK: dodecyl dimethyl benzyl ammonium chloride; PA: phosphoric acid; AA: acetic acid; STPP: sodium tripolyphosphate; CPC: hexadecyl pyridinium chloride; DDAC: didecyl dimethyl ammonium chloride; PPP: potassium pyrophosphate; PHMB: polyhexamethylene biguanide hydrochloride.

The above description only shows the preferred embodiments of the present disclosure and is not intended to limit the present disclosure. All the modifications, equivalent replacements, improvements, and the like within the spirit and the principle of the present disclosure, are supposed to be contained in the scope of protection of the present disclosure.

What is claimed is:

1. A method for removing a smear layer on root canal, comprising treating the root canal with a citrate metal salt, wherein the citrate metal salt is lithium citrate, sodium citrate, potassium citrate, or magnesium citrate, wherein the citrate metal salt is formulated into a liquid, paste or gel with a pH value of 5.5-7.0, and wherein the citrate metal salt constitutes 5%-25% by mass percentage of the liquid, paste or gel.

2. The method according to claim 1, wherein a single-chain cationic antibacterial agent compatible with the citrate metal salt is further added to co-formulate into a liquid, paste or gel.

3. The method according to claim 2, wherein the single-chain cationic antibacterial agent is one of, or a mixture of any of, dodecyl to hexadecyl pyridinium chloride, polydimethyl diallyl ammonium chloride, decyl to hexadecyl dimethyl benzyl ammonium chloride, decyl to hexadecyl dimethyl benzyl ammonium bromide, decyl to octadecyl dimethyl benzyl ammonium bromide, or decyl to octadecyl trimethyl ammonium chloride.

4. The method according to claim 1, wherein a pH regulator is added to the liquid, paste, or gel to adjust the pH value of the liquid, paste or gel to 5.5-7.0.

5. A formulation for removing a smear layer, wherein the formulation is a liquid, paste or gel with a pH value of 5.5-7.0 and is mainly formulated from a citrate metal salt, and the citrate metal salt is lithium citrate, sodium citrate, potassium citrate or magnesium citrate, and wherein the citrate metal salt constitutes 5%-25% by mass percentage of the formulation.

6. The formulation according to claim 5, wherein the formulation comprises a single-chain cationic antibacterial agent compatible with the citrate metal salt, and the single-chain cationic antibacterial agent is one of, or a mixture of any of, dodecyl to hexadecyl pyridinium chloride, polydimethyl diallyl ammonium chloride, decyl to hexadecyl dimethyl benzyl ammonium chloride, decyl to hexadecyl dimethyl benzyl ammonium bromide, decyl to octadecyl dimethyl benzyl ammonium bromide, or decyl to octadecyl trimethyl ammonium chloride.

7. The formulation according to claim 5, wherein the formulation consists of the following components: by mass percentage, 5%-25% of citrate metal salt, 0-5% of single-chain cationic antibacterial agent compatible with the citrate metal salt, with the balance of a solvent and/or an excipient.

8. A method of using the formulation according to claim 7, wherein the formulation is applied to root canal to remove the smear layer for an application time of no more than 10 minutes.

* * * * *